(12) United States Patent
Ebert

(10) Patent No.: US 6,952,261 B2
(45) Date of Patent: Oct. 4, 2005

(54) SYSTEM FOR PERFORMING ELLIPSOMETRY USING AN AUXILIARY PUMP BEAM TO REDUCE EFFECTIVE MEASUREMENT SPOT SIZE

(75) Inventor: Martin Ebert, Fremont, CA (US)

(73) Assignee: Therma-Wave, Inc., Fremont, CA (US)

( * ) Notice: Subject to any disclaimer, the term of this patent is extended or adjusted under 35 U.S.C. 154(b) by 228 days.

(21) Appl. No.: 10/403,489

(22) Filed: Mar. 31, 2003

(65) Prior Publication Data

US 2004/0189993 A1 Sep. 30, 2004

(51) Int. Cl.$^7$ ............................................. G01J 4/00
(52) U.S. Cl. ........................................................ 356/369
(58) Field of Search .............................. 356/364–369, 356/237–237.5

(56) References Cited

U.S. PATENT DOCUMENTS

| | | | |
|---|---|---|---|
| 4,579,463 A | 4/1986 | Rosencwaig et al. | 374/57 |
| 4,636,088 A | 1/1987 | Rosencwaig et al. | 374/5 |
| 4,652,757 A | 3/1987 | Carver | 250/360.1 |
| 5,596,411 A | 1/1997 | Fanton et al. | 356/369 |
| 5,978,074 A | 11/1999 | Opsal et al. | 356/72 |
| 6,268,916 B1 * | 7/2001 | Lee et al. | 356/369 |
| 2004/0169859 A1 * | 9/2004 | Smith | 356/369 |

OTHER PUBLICATIONS

G.E. Carver et al., "Applications of Optical Beam–Induced Reflectance Scans in Silicon Processing," *IEEE Journal of Quantam Electronics*, vol. 25, No. 5, May 1989, pp. 1079–1085.

G.E. Carver et al., "Non–Destructive Optical Techniques for Characterizing Semiconductor Materials and Devices," *AT&T Technical Journal*, Mar./Apr. 1994, pp. 66–76.

\* cited by examiner

*Primary Examiner*—Layla Lauchman
(74) *Attorney, Agent, or Firm*—Stallman & Pollock LLP

(57) ABSTRACT

An ellipsometer includes a light source for generating a probe beam of polychromatic light for interacting with a sample. The probe beam is passed through a first polarizer that imparts a known polarization state to the probe beam. The polarized probe beam is then directed to reflect from the sample. A second illumination source is switched on and off at a predetermined frequency to create an intensity modulated pump beam (the beam may also be chopped). The pump beam is directed normally against the subject producing a small illumination spot within the area illuminated by the probe beam. The pump induces localized changes in the dielectric properties of the subject. The pump-beam induced oscillations are picked up by the portion of the probe beam that is reflected from within the illumination spot of the pump beam. By analyzing only the portion of the reflected probe beam that includes the pump beam induced oscillation, the size of the measurement spot is effectively limited to the illumination spot size of the normally directed pump beam.

3 Claims, 1 Drawing Sheet

SYSTEM FOR PERFORMING ELLIPSOMETRY USING AN AUXILIARY PUMP BEAM TO REDUCE EFFECTIVE MEASUREMENT SPOT SIZE

TECHNICAL FIELD

The subject invention relates to ellipsometry systems used to inspect and analyze semiconductor wafers. In particular, this invention relates to ellipsometry systems that operate using small measurement spot sizes.

BACKGROUND OF THE INVENTION

As geometries continue to shrink, manufacturers have increasingly turned to optical techniques to perform non-destructive inspection and analysis of semi-conductor wafers. The basis for these techniques is the notion that a subject may be examined by analyzing the reflected energy that results when a probe beam is directed at the subject. Ellipsometry and reflectometry are two examples of commonly used optical techniques. For the specific case of ellipsometry, changes in the polarization state of the probe beam are analyzed. Reflectometry is similar, except that changes in magnitude of the reflected intensities are analyzed. Scatterometry is a related technique that measures the diffraction (optical scattering) that the subject imparts to the probe beam.

Techniques of this type may be used to analyze a wide range of attributes. This includes film properties such as thickness, crystallinity, composition and refractive index. Typically, measurements of this type are made using reflectometry or ellipsometry as described more fully in U.S. Pat. Nos. 5,910,842 and 5,798,837 both of which are incorporated in this document by reference. Critical dimensions (CD) including line spacing, line width, wall depth, and wall profiles are another type of attributes that may be analyzed. Measurements of this type may be obtained using monochromatic scatterometry as described in U.S. Pat. Nos. 4,710,642 and 5,164,790 (McNeil). Another approach is to use broadband light to perform multiple wavelength spectroscopic reflectometry measurements. Examples of this approach are found in U.S. Pat. No. 5,607,800 (Ziger); U.S. Pat. No. 5,867,276 (McNeil) and U.S. Pat. No. 5,963,329 (Conrad) (each of the patents is incorporated in this document by reference). Still other tools utilize spectroscopic ellipsometric measurement. Examples of such tools can be found in U.S. Pat. No. 5,739,909 (Blayo) and U.S. Pat. No. 6,483,580 (Xu). Each of these patents and publications are incorporated herein by reference.

Photo-modulated reflectance (PMR) is another technique used to perform non-destructive inspection and analysis of semi-conductor wafers. As described in U.S. Pat. No. 4,579,463 (incorporated in this document by reference), PMR-type systems use a combination of two separate optical beams. The first of these, referred to as the pump beam is created by switching a laser on and off. The pump beam is projected against the surface of a subject causing localized heating of the subject. As the pump laser is switched, the localized heating (and subsequent cooling) creates a train of thermal waves in the subject. The second optical beam, referred to as the probe beam is directed at a portion of the subject that is illuminated by the pump laser. The thermal waves within the subject alter the reflectivity of the subject and, in turn, the intensity of the reflected probe beam. A detector synchronously samples the reflected probe beam synchronously with the switching frequency of the pump laser. The resulting output is used to evaluate parameters such as film thickness and material composition.

The article "Applications of Optical Beam-Induced Reflectance Scans in Silicon Processing" (Gary E. Carver and John D. Michalski, *IEEE Journal of Quantum Electronics*, Vol. 25, No. 5 1989) discloses a second type of optical metrology system that uses a laser-generated pump beam. For this second system, an off-axis probe beam intersects the subject at a relatively large angle of incidence. The pulsed pump is directed normally to the subject and modulates the intensity of the reflected probe beam. The modulated intensities are used to evaluate the subject. The authors have reported that this combination results in an enhanced sensitivity to near-surface electrically active defects.

As the geometries used in semiconductors continue to decrease, optical metrology tools are forced to analyze smaller and smaller structures. For most optical metrology systems, this means using smaller measurement spots (the area within a subject that the detected light originates from during measurement). At the same time, it is not always practical to reduce measurement size, particularly for ellipsometers. This is partially because ellipsometers are typically configured to operate at non-normal angles of incidence (unlike reflectometers and the some of the PMR-type systems described above). The non-normal angle of incidence increases sensitivity to thin-film properties. At the same time, non-normal incidence elongates the measurement spot by a factor equal to $1/\cos(\theta)$ where $\theta$ is the angle of incidence. For an incident angle of seventy-degrees, for example, this elongation means that the measurement spot is spread to nearly three times its normal length.

Chromatic aberration is a second obstacle that often limits reductions in measurement spot sizes for ellipsometers. Chromatic aberration results when an optical system transports light in a wavelength dependent fashion. In spectral ellipsometers, the probe beam includes a range of wavelengths and chromatic aberration tends to create different measurement spot sizes for the different probe beam wavelengths. This is particularly true for spectral ellipsometers that use diffractive optical elements. The overall result is that the minimum size of the measurement spot is influenced by the range of wavelengths included in the probe beam and the amount of chromatic aberration present of the spectral ellipsometer.

One approach for reducing measurement spot sizes in ellipsometers is to use high numerical aperture lenses to perform measurement spot imaging. This is described, for example, in U.S. Pat. No. 5,596,411 (incorporated in this document by reference). The use of the high numerical aperture lens increases the accuracy with which the measurement spot may be imaged. The high numerical lens also creates a spread of angles of incidence all converging on a relatively small illumination spot. For some applications, the multiple angle of incidence approach provides an enhanced ability to deduce properties of the sample being analyzed. At the same time, the use of multiple angles of incidence increases the difficulty (i.e., computational complexity) of interpreting the resulting measurements. In some cases, this can make this particular approach impractical.

A second approach for reducing measurement spot sizes in ellipsometers is described in U.S. patent application Ser. No. 10/319,189, filed Mar. 13, 2002 (incorporated in this document by reference). For this approach, a shallow (or near normal) angle of incidence is used to produce a relatively small measurement spot size. In combination with the shallow angle of incidence, a rotating compensator is used to impart a wavelength dependent phase delay to the probe beam. A detector translates the reflected probe beam into a signal that includes DC, 2ω and 4ω signal components (where ω is the angular velocity of the rotating compensator). A processor analyzes the signal using the DC, 2ω and 4ω components. The use of the DC component allows thin film characteristics to be accurately analyzed without the need for larger angles of incidence. At the same time, the use of normal or near normal incidence has a tendency to reduce or eliminate the distinction between p and s polarized light and may make this approach unsuitable for some applications.

Based on the preceding description, it is clear that there is a continual need to produce ellipsometers that operate using smaller and smaller measurement spots. This need is particularly true for semiconductor manufacturing where structure sizes continue to decrease.

SUMMARY OF THE INVENTION

An aspect of the present invention provides an ellipsometer that produces an effectively small measurement spot even when operating at large angles of incidence. For a representative implementation, the ellipsometer includes a first illumination source that creates a probe beam. The probe beam may be monochromatic or, more typically, polychromatic. The probe beam is passed through a first polarizer that imparts a known polarization state to the probe beam. The polarized probe beam is then directed to reflect from the sample. The angle of incidence between the incoming probe beam and the sample is implementation dependent. In most cases, this angle will be non-zero and may be relatively large (e.g. seventy-degrees). The reflected probe beam passes through a rotating compensator (if present) and then through a second polarizer (analyzer).

A second illumination source (typically monochromatic) is used to create an intensity modulated pump beam. For typical implementations, the second illumination source is switched on and off to create the required modulation, but there may be implementations where partial power levels are used. Different switching patterns may be used to control the waveform of the pump beam (i.e., pulse width, pulse shape and interpulse period). The pump beam may also be chopped or otherwise processed to produce the same effect. The pump beam is focused by one or more lenses and/or mirrors and directed normally (or close to normal) against the subject producing a small illumination spot. The illumination spot of the pump beam is positioned inside of the area illuminated by the probe beam.

The modulated pump beam introduces localized oscillations in the optical properties of the subject. This creates a corresponding oscillation in the portion of the probe beam that is reflected from within the illumination spot of the pump beam. By analyzing only the portion of the probe beam that includes the pump beam induced oscillations, the size of the measurement spot is reduced to match the size of the pump beam illumination spot.

DETAILED DESCRIPTION OF THE PREFERRED EMBODIMENTS

Figure 1:
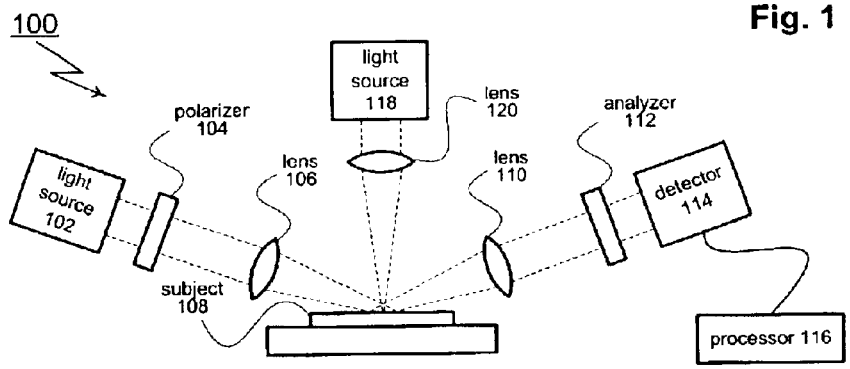
FIG. 1 is a block diagram of an ellipsometer as provided by an aspect of the present invention.

As shown in FIG. 1, an aspect of the present invention includes an ellipsometer generally designated 100. Ellipsometer 100 includes a first illumination source 102 that creates a mono or polychromatic probe beam. The probe beam is passed through a polarizer 104 and focused by one or more lenses 106 (or other appropriate optical elements such as mirrors). Polarizer 104 imparts a known polarization state to the probe beam. The polarized probe beam creates an illumination spot on the surface of the subject under test 108. An image of the illumination spot (or a portion of the illumination spot) passes through one or more lenses 110 and an analyzer 112 before reaching a detector 114. Lenses 110 may be selected from a range of different components including achromatic lenses and focusing mirrors. Detector 114 captures (or otherwise processes) the received image. A processor 116 analyzes the data collected by the detector 114.

Ellipsometer 100 also includes a second illumination source 118. Second illumination source 118 creates an intensity modulated pump beam that is, for typical implementations, monochromatic. For other applications, the pump beam may be polychromatic. The pump beam is passed though one or more lenses 120 (or other optical elements) before reaching subject 108.

Figure 2:
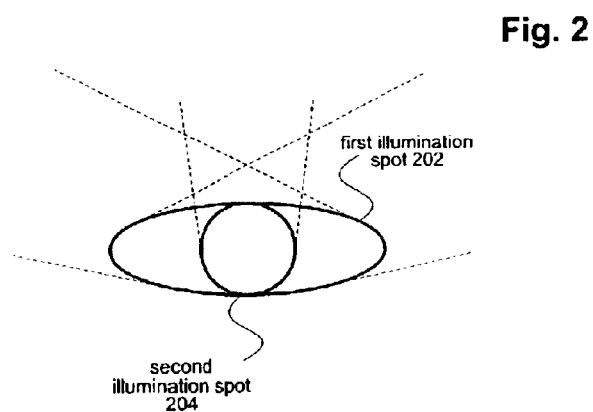
FIG. 2 shows the two illumination spots produced by the ellipsometer of FIG. 1.

As shown in FIG. 2, ellipsometer 100 produces two illumination spots. The first illumination spot is labeled 202 and is created by the probe beam. First illumination spot 202 has an elliptical shape caused by the off-axis orientation of the probe beam. For the particular example of FIG. 2, illumination spot 202 has a major radius that is approximately three times as large as its minor radius. This corresponds to the case shown in FIG. 1 where the probe beam has an angle of incidence equal to seventy degrees.

The second illumination spot is labeled 204 and is created by the pump beam. The normal (or substantially normal) incidence of the pump beam gives second illumination spot 204 a substantially circular shape. For optimal efficiency, second illumination spot 204 has a radius equal to the minor radius of first illumination spot 202 (i.e., second illumination spot 204 spans first illumination spot 202).

Second illumination source 118 is controlled to modulate the intensity of the pump beam. Typically, this means that second illumination source 118 is switched on and off, but there may be implementations where partial power levels are used. Different switching patterns may be used to control the waveform (i.e., pulse width, pulse shape and interpulse period) of the pump beam. Alternately, it is possible to maintain the output of second illumination source 118 at a fixed level and use a chopper or other optical elements to create the desired waveform.

The pump beam causes the optical properties of the subject to oscillate. The oscillation is localized within second illumination spot 204 and is synchronized to the modulation of the pump beam. The pump-beam induced oscillations are picked up by the portion of the probe beam that is reflected from within second illumination spot 204. As a result, the reflected probe beam includes a component that oscillates in synchronicity with the modulation of the pump beam.

Processor 116 includes a synchronizing input (not shown) that allows it to analyze the input of detector 114 in light of the modulations of the pump beam. During this analysis, processor 116 uses the synchronizing input to identify the portion of the received probe beam that includes the pump beam induced oscillations. By analyzing only that portion, the size of the measurement spot is effectively limited to the size of second illumination spot 204.

Figure 3:
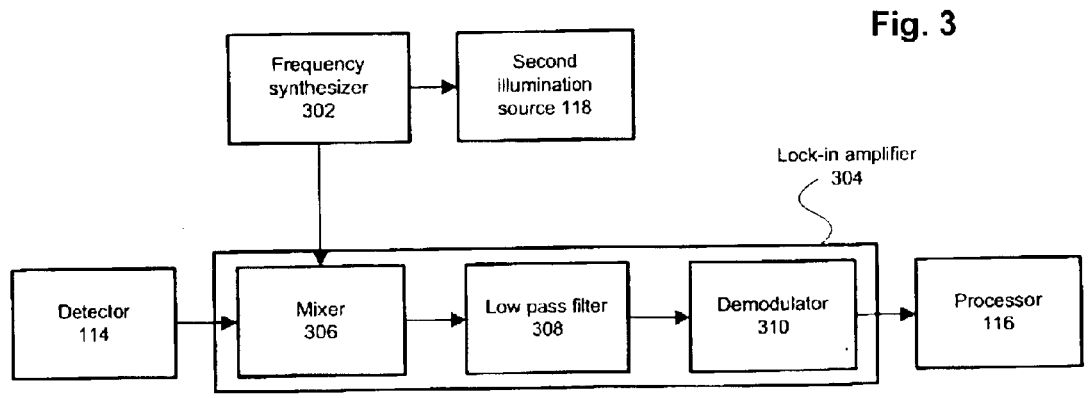
FIG. 3 shows a lock-in amplifier for use with the ellipsometer of FIG. 1.

In some cases, the switching frequency of the pump beam may be quite high. As a result, it is generally desirable to perform some form of heterodyne mixing to reduce the frequency of the signal analyzed by processor 116. Mixing of this type is described in U.S. Pat. No. 5,978,074, incorporated herein by reference. As shown in FIG. 3, an implementation for electronic heterodyne mixing includes a frequency generator 302 that sends a switching frequency to control second illumination source 118. Second illumination source 118 uses the switching frequency to clock the modulation frequencies included in the pump beam.

Frequency generator 302 also sends a heterodyne signal to a lock-in amplifier 304. The heterodyne signal will be close to, but different from the signal sent to second illumination source 118. For example, the heterodyne signal can be 10 KHz higher than the signal sent to second illumination source 118.

The heterodyne signal from frequency generator 302 is combined with the output from detector 114 in a mixer 306. The output of mixer 306 includes signal components at both the sum and difference of its two input signals. The difference signal will be at the relatively low frequency of 10 KHz (for the specific example where the heterodyne signal is 10 KHz higher or lower than the signal sent to second illumination source 118). All the signals are passed through a low pass filter 308 to eliminate the high frequency components from frequency generator 302 and detector 114.

The resulting low frequency signal is then demodulated by a demodulator 310. The outputs of demodulator 310 are the "in-phase" and "quadrature" signals typical of a lock-in amplifier. The in-phase and quadrature signals can be used by processor 116 to calculate the magnitude and the phase of the modulated optical reflectivity signal.

As an alternative to using an electronic heterodyne downmixing system, it is also possible to reduce the frequency of detection using an optical heterodyne approach. Such an optical approach is disclosed in U.S. Pat. No. 5,408,327, incorporated herein by reference. In this system, two laser beams are directed at the surface of a subject. The beams are modulated at slightly different frequencies. The beam from one laser picks up an intensity modulation upon reflection due to the modulated optical reflectivity induced in the sample by the other beam. The intensity modulated signal picked up upon reflection "mixes" with the inherent modulation of the beam, creating additional modulations in the beam at both the sum and difference frequency. This process is analogous to electrical heterodyning. The difference or "beat" frequency is much lower than either of the initial beam modulation frequencies and can therefore be detected by a low frequency lock-in amplifier. For the case of ellipsometer 100, optical heterodyne down-mixing may be accomplished using two (or more) pump beams or by modulating the intensity of the pump and probe beams.

What is claimed is:

1. An ellipsometric method for evaluating a sample comprising the steps of:

generating a polarized probe beam;

directing the probe beam to produce an illumination spot on the sample;

generating an intensity modulated pump beam;

directing the pump beam to cause the reflectivity of a portion of the illumination spot to oscillate in synchronicity with the modulations of the pump beam;

collecting light reflected from the illumination spot;

selecting a portion of the collected light that exhibits oscillations in intensity that are synchronized with the modulations of the pump beam; and evaluating the sample by analyzing polarity phase differences between the generated probe beam and the selected portion.

2. An ellipsometric method for evaluating a sample comprising the steps of:

generating a polarized probe beam;

directing the probe beam to produce an illumination spot on the sample;

modulating the dielectric properties of the sample where the modulation is localized to a portion of the area covered by the illumination spot;

collecting light reflected from the illumination spot; and selecting a portion of the collected light that exhibits oscillations in electromagnetic properties that correspond to the modulation applied to the sample;

evaluating the sample by analyzing polarity phase differences between the probe beam as generated and the selected portion.

3. An ellipsometer for evaluating a sample comprising:

a probe beam directed to the sample at a non-normal angle of incidence and defining an illuminated spot on the surface thereof;

a photodetector for measuring the intensity of the probe beam after interaction with the sample;

an intensity modulated pump beam;

optics for focusing the pump beam to a pump spot within and smaller than the illuminated spot; and a processor for determining the changes in the polarization state of the probe beam induced by interaction with the sample and wherein those changes are synchronous with the modulation frequency of the pump beam and evaluating the sample based on the determined changes.

* * * * *